United States Patent
Czech

(10) Patent No.: US 6,475,568 B1
(45) Date of Patent: Nov. 5, 2002

(54) BLOCK, NON-(AB)$^N$ SILICONE POLYALKYLENEOXIDE COPOLYMERS WITH TERTIARY AMINO LINKS

(75) Inventor: Anna Maria Czech, Cortlandt Manor, NY (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 09/854,583

(22) Filed: May 15, 2001

(51) Int. Cl.$^7$ ................................................. B05D 7/00
(52) U.S. Cl. ........................ 427/386; 556/444; 556/445; 528/28; 528/27; 8/127.5; 8/128.3; 424/70.12; 427/389.9; 427/389; 427/387
(58) Field of Search ........................ 556/444, 445; 528/28, 27; 8/128.3, 127.5; 424/70.12; 427/389.9, 389, 386, 387

(56) References Cited

U.S. PATENT DOCUMENTS

| | | | |
|---|---|---|---|
| 3,761,444 A | 9/1973 | Medocino | 260/46.5 |
| 4,101,272 A | 7/1978 | Guise et al. | 8/127.6 |
| 4,242,466 A | 12/1980 | Schilling, Jr. et al. | 521/112 |
| 4,409,267 A * | 10/1983 | Ichinohe et al. | |
| 4,833,225 A | 5/1989 | Schaefer et al. | 528/28 |
| 5,807,956 A | 9/1998 | Czech | 528/28 |
| 5,981,681 A | 11/1999 | Czech | 528/27 |

FOREIGN PATENT DOCUMENTS

| | | |
|---|---|---|
| DE | 19817776 | 4/1998 |
| GB | 1213779 | 11/1970 |

* cited by examiner

*Primary Examiner*—Robert Dawson
*Assistant Examiner*—Kuo-Liang Peng
(74) *Attorney, Agent, or Firm*—Michael P. Dilworth

(57) ABSTRACT

A composition is disclosed that comprises non-hydrolyzable, block, non-(AB)$_n$ type copolymers comprising units of the formula $\{XR^2[(SiO(R^1)_2]_xSi(R^1)_2R^2X\}$, units of the formula $\{YO(C_aH_{2a}O)_bY\}$, and linking groups —NR$^3$—, wherein R$^1$ is alkyl, R$^2$ is a divalent organic moiety, X and Y are independently selected divalent organic groups formed by the ring opening of an epoxide, R$^3$ is selected from the group consisting of alkyl, aryl, aralkyl, oxygen-containing alkyl, oxygen-containing aryl, and oxygen-containing aralkyl, a=2 to 4, b=2 to 100, and x=1 to 500.

27 Claims, No Drawings

BLOCK, NON-(AB)$^N$ SILICONE POLYALKYLENEOXIDE COPOLYMERS WITH TERTIARY AMINO LINKS

BACKGROUND OF THE INVENTION

1. Field of the Invention

The present invention relates to novel block, non-(AB)$_n$, linear copolymers comprising units of polysiloxane and polyalkyleneoxide linked by tertiary amino groups, a method for the preparation of these copolymers, and to the use of these copolymers as conditioning ingredients in hair care and skin care products and as textile softeners, particularly, re-wettable textile softeners.

2. Description of Related Art

Examples of non-hydrolyzable siloxane-polyalkyleneoxide block copolymers are known in the prior art.

U.S. Pat. No. 3,761,444 discloses an improvement in the manufacture of epoxy substituted siloxanes. Lower molecular weight epoxy substituted siloxanes are equilibrated with other siloxanes to produce siloxane copolymers containing the substituents of both the epoxy siloxane and the other siloxanes. This is accomplished with a basic equilibration catalyst and in the presence of small quantities of water and silanol.

U.S. Pat. No. 4,101,272 discloses a process for the treatment of fibrous materials to improve their properties, in which the fibrous materials are treated with a composition containing: a component A selected from the class consisting of polyorganosiloxanes of the general formula

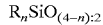

$$R_nSiO_{(4-n):2}$$

in which n has an average value in the range 1.8 to 2.2, and R represents organic radicals attached to the silicon atoms by carbon-silicon bonds; wherein between 1.0 and 50 percent of the radicals R consist of one or more organic radicals containing an epoxide group and selected from the class consisting of: 1,2-epoxyethyl; 3,4-epoxycyclohexyl; 6-methyl-3,4-epoxycyclohexyl; 3,4-epoxycyclohexyl-1-ethyl; 9,10-epoxystearyl; 3-(2,3-epoxypropoxy)propyl; p-(2,3-epoxybutyl)-phenyl; and 3-(3,4-epoxybutyl) cyclohexyl, and the remainder of the radicals R consist of one or more organic radicals selected from the class consisting of alkyl and aryl radicals; and a polyamine component B which consists of one or more organic compounds each with two or more primary and/or secondary amino groups attached to aliphatic carbon atoms such that there are at least 5 carbon atoms per amino group, or two or more groups capable of providing, by reaction, primary and/or secondary amino groups; and allowing the components A and B to react chemically.

U.S. Pat. No. 4,242,466 discloses organic ethers including polyethers having two $CH_2=C(R)CH_2-$ end groups per molecule wherein R is a monovalent hydrocarbon group that are reacted with organohydrosiloxanes under hydrosilation reaction conditions in the presence of a platinum catalyst to form nonhydrolyzable siloxane block copolymers. Non-hydrolyzable linear block copolymers substantially free of silicon-bonded hydrogen are obtained with linear dihydropolyorganosiloxane reactants and linear ethers or polyethers.

U.S. Pat. No. 4,833,225 discloses polyquaternary polysiloxane polymers having defined repeating units. The compounds may be synthesized by an addition reaction between an α,ω-hydrogenpolysiloxane of a given formula and epoxides which have a terminal olefinic bond, and reacting the product obtained with a diamine. The polymers may be used in cosmetic preparations, especially in hair cosmetics.

U.S. Pat. Nos. 5,807,956 and 5,981,681 disclose non-hydrolyzable, block, (AB)$_n$A type, copolymers comprising alternating units of polysiloxane and amino-polyalkyleneoxide and provide a method for the preparation of these copolymers. Also provided is the use of these copolymers as softeners, in particular durable, hydrophilic textile softeners, which improve tactile properties of the textiles substrates treated with the commercial soil release finishes, without substantially detracting from their properties. The copolymers have alternating units of polysiloxane $[X(C_aH_{2a}O)_bR^2[(SiO(R^1)_2]_cSi(R^1)_2R^2(C_aH_{2a}O)_bX]$ and polyalkyleneoxides $[YO(C_aH_{2a}O)_dY]$ wherein $R^1$ is a $C_1$ to $C_4$ alkyl, preferably methyl, $R^2$ is a divalent organic moiety, X and Y are divalent organic groups selected from a secondary or tertiary amine and a ring opened epoxide, such that when X is a ring opened epoxide, Y is an amine and vice versa, a=2 to 4, preferably 2 to 3, b=0 to 100, d=0 to 100, b+d=1 to 100, preferably 10 to 50, and c=1 to 500, preferably 10 to 100.

U.K. Patent No. 1,213,779 discloses a process for the production of an organo-silicon compound by the addition of a hydrogen-silane or -siloxane to an olefinically-unsaturated organic compound in the presence of a catalyst, trimethyl-dipyridine-platinum-iodide.

DE 19817776 A1 provides another example of the (AB)$_n$ aminopolysiloxane polyalkylyneoxide copolymers. These copolymers are derived from reaction of the acrylate terminated polyether with amine terminated polysiloxanes under Michael's addition conditions.

The disclosures of the foregoing are incorporated herein by reference in their entirety.

SUMMARY OF THE INVENTION

The present invention is directed to non-hydrolyzable, block, non-(AB)$_n$ type copolymers comprising units of polydimethylsiloxane and polyalkyleneoxide linked by tertiary amino groups.

In another aspect, the present invention is directed to a method for the preparation of these copolymers from the epoxy terminated polydimethylsiloxanes and epoxy terminated polyalkyleneoxides with primary amines or a combination of primary and secondary amines, where secondary amine functions as a chain stopper.

In still another aspect, the present invention is directed to the use of these copolymers as conditioning ingredients for hair care and skin care, as well as textile softeners to improve wettability and tactile properties of textile substrates.

More particularly, the present invention is directed to a composition comprising non-hydrolyzable, block, non-(AB)$_n$ type copolymers comprising units of the formula $\{XR^2[(SiO(R^1)_2]_xSi(R^1)_2R^2X\}$, units of the formula $\{YO(C_aH_{2a}O)_bY\}$, and linking groups $-NR^3-$, wherein $R^1$ is alkyl, $R^2$ is a divalent organic moiety, X and Y are independently selected divalent organic groups formed by the ring opening of an epoxide, $R^3$ is selected from the group consisting of alkyl, aryl, aralkyl, oxygen-containing alkyl, oxygen-containing aryl, and oxygen-containing aralkyl, a=2 to 4, b=2 to 100, and x=1 to 500.

In another embodiment, the present invention is directed to a method of making non-hydrolyzable, block, non-(AB)$_n$ type copolymers comprising units of the formula $\{XR^2[(SiO(R^1)_2]_xSi(R^1)_2R^2X\}$, units of the formula $\{YO(C_aH_{2a}O)$ $_bY\}$, and linking groups —$NR^3$—, wherein $R^1$ is alkyl, $R^2$ is a divalent organic moiety, X and Y are independently selected divalent organic groups formed by the ring opening of an epoxide, $R^3$ is selected from the group consisting of alkyl, aryl, aralkyl, oxygen-containing alkyl, oxygen-containing aryl, and oxygen-containing aralkyl, a=2 to 4, b=2 to 100, and x=1 to 500, wherein the method comprises reacting (1) polysiloxanes of the formula $QR^2[(SiO(R^1)_2]_xSi(R^1)_2R^2Q$, and (2) polyalkyleneoxides of the formula $\{ZO(C_bH_{2b}O)_dZ\}$, wherein Q and Z are epoxide containing groups, with at least one primary amine or a combination of primary and secondary amines.

In still another embodiment, the present invention is directed to a method for softening a substrate comprising applying to said substrate a composition comprising non-hydrolyzable, block, non-(AB)$_n$ type copolymers comprising units of the formula $\{XR^2[(SiO(R^1)_2]_xSi(R^1)_2R^2X\}$, units of the formula $\{YO(C_aH_{2a}O)_bY\}$, and linking groups —$NR^3$—, wherein $R^1$ is alkyl, $R^2$ is a divalent organic moiety, X and Y are independently selected divalent organic groups formed by the ring opening of an epoxide, $R^3$ is selected from the group consisting of alkyl, aryl, aralkyl, oxygen-containing alkyl, oxygen-containing aryl, and oxygen-containing aralkyl, a=2 to 4, b=2 to 100, and x=1 to 500.

DESCRIPTION OF THE PREFERRED EMBODIMENTS

A. Copolymer Structure

The block copolymers of the present invention have in their structure polysiloxane units $\{XR^2[(SiO(R^1)_2]_xSi(R^1)_2R^2X\}$, polyalkyleneoxide units $\{YO(C_aH_{2a}O)_bY\}$ and linking groups —$NR^3$—, wherein $R^1$ is alkyl, $R^2$ is a divalent organic moiety, X and Y are divalent organic groups formed by the ring opening of an epoxide, $R^3$ is selected from the group consisting of alkyl, aryl, aralkyl, oxygen-containing alkyl, oxygen-containing aryl, and oxygen-containing aralkyl, a=2 to 4, b=2 to 100, preferably 3 to 50, x=1 to 500, preferably 150.

$R^1$ is preferably lower alkyl, e.g., an alkyl having from one to four carbon atoms, i.e., methyl, ethyl, propyl, butyl, and isomers of the foregoing, e.g., isopropyl, t-butyl, and the like. More preferably, $R^1$ is methyl.

$R^2$ is preferably a divalent hydrocarbon group with at least one carbon, which may have hydroxy substitutions thereon and/or include an ether linkage. Preferably, it contains less than ten carbon atoms. Within a particular molecule, each $R^1$, $R^2$, $R^3$ and $R^4$ may be the same or different.

The copolymers are preferably end-capped with secondary amino groups —$NHR^3$ or tertiary groups —$NR^3R^4$, where $R^4$ is also chosen from the group consisting of alkyl, aryl, aralkyl, oxygen-containing alkyl, oxygen-containing aryl, and oxygen-containing aralkyl, and where $R^3$ and $R^4$ can be the same or different.

The moieties comprising $R^3$ and $R^4$ preferably comprise from one to about twenty carbon atoms, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxy, ethoxy, propoxy, butoxy, phenyl, biphenyl, naphthyl, tolyl, xylyl, anthracyl, methoxyphenyl, isomers of the foregoing, and the like.

The copolymers are not (AB)$_n$ type because blocks may consist of more than one unit, therefore the nominal length of the blocks will vary. Moreover, blocks comprising more than one unit will be interrupted with the amino groups. The number of units per molecule is limited by the ability to handle high viscosity material, since the viscosity is directly proportional to the number of units, but practically there should be at least two of each unit and may be up to 1,000 units. It is preferred that the terminal groups of the copolymer be amino groups, as noted above.

The molecular weight of the copolymers can be modified by varying the molar ratio of the epoxy component to amino component, by varying the number of oxyalkylene units and the number of siloxy groups within the polysiloxane blocks.

The ring-opened epoxides, represented by either X or Y, may be aliphatic, cycloaliphatic, and may contain aromatic rings. They also contain hydroxy groups and may contain an ether linkage. Preferably, the ring-opened epoxide is chosen from the following: —$CH_2CH(OH)(CH_2)_vCH(OH)CH_2$—, —$CH[CH_2OH](CH_2)_vCH[CH_2OH]$—, —$CH_2CH(OH)(CH_2)_vCH[CH_2OH]$—, —$(CH_2)_v$—$OCH_2CH(OH)CH_2$—; —$(CH_2)_vOCH_2CH(CH_2[OH])$— with v=2 to 6. Alternatively, the ring-opened epoxides may be derived from the following epoxycyclohexyl alkylene groups, ω-(3,4-epoxycyclohexyl)alkylene, β-(3,4-epoxycyclohexyl)ethylene, β-(3,4-epoxycyclohexyl)-β-methylethylene, and β-(3,4-epoxy-4-methylcyclohexyl)-β-methylethylene.

The polyoxyalkylene blocks represented by $(C_aH_{2a}O)$ or $(OC_aH_{2a})$ may be made up of ethylene oxide (a=2), propylene oxide (a=3), and butylene oxide (a=4) in a random or blocked fashion. The ratio among such oxides is not of particular importance, but may be adjusted as required for the desired solubility parameters of the resulting copolymer.

B. Method of Manufacture

The compounds of the present invention are prepared by reacting two species:

(1) polysiloxanes $QR^2[(SiO(R^1)_2]_xSi(R^1)_2R^2Q$, and (2) polyalkyleneoxides $[ZO(C_bH_{2b}O)_dZ]$, which are the same as the formulae above except that Q and Z are epoxide containing groups, with a primary amine or a combination of primary and secondary amines, where the secondary amine will function as a chain stopper. These species may be manufactured by means known in the art or are commercially available.

In an exemplary process, α,ω-hydrogenpolysiloxanes of the general formula $H(SiO(R^1)_2)_xSi(R^1)_2H$ are reacted in a first step with the unsaturated epoxides with a terminal olefinic bond, such as allyl glycidyl ether, in the presence of a hydrosilation catalyst, such as hexachloroplatinic acid, at elevated temperature, to produce epoxy end-blocked polysiloxanes. Such procedures are known in the art as indicated in U.S. Pat. No. 3,761,444 and U.K. Patent No. 1,213,779. The following are examples of suitable epoxides with terminal olefinic groups.

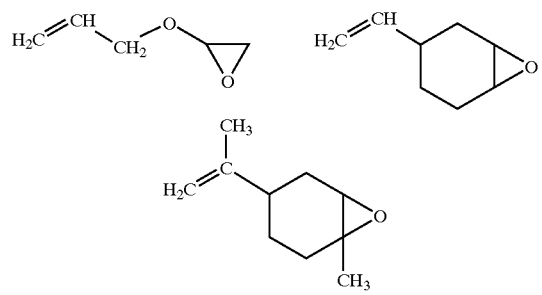

In a second step, the epoxy end-blocked polysiloxanes and epoxy end-blocked polyalkyleneoxides are reacted with primary amino groups or a combination of primary and secondary amino groups. Suitable epoxy end-blocked polyalkyleneoxides are represented, for example, by DER 732 and DER 736 available from Dow Chemical Co. The primary amines may, for example, be selected from ethylamine, propylamine, butylamine, isobutylamine, hexylamine, cyclohexylamine, benzylamine, ethanolamine, propanolamine, and the like, the secondary amines may be selected, for example, from diethylamine, dipropylamine, dibutylamine, diisobutylamine, dihexylamine, dicyclohexylamine, dibenzylamine, diethanolamine, dipropanolamine, and the like. The reaction is carried out in a suitable solvent, such as an alcohol or a mixture of alcohol and water at reflux. If the boiling point of the amine is lower than the boiling point of the solvent, the reaction is conducted in a pressurized vessel. Typically, the epoxy end-blocked polysiloxanes and epoxy end-blocked polyalkyleneoxides are added to the solution of the amine in the reaction solvent.

For practical purposes, the reaction is carried out with about a 1 to to about 30 percent, preferably about 1 to about 20 percent, excess of the amine-containing species. Despite using an excess of the amine used during the preparation of the copolymers whereby the majority of the end-groups can be expected to be amines, it is possible that the epoxy end group on the polysiloxane can undergo side reactions with the solvent, water, or alcohol to form the corresponding diol or ether alcohol.

After the reaction, the solution of the copolymer can be neutralized by a direct addition of a Brönsted acid, such as acetic acid, citric acid, tartaric acid, or fatty acids, such as stearic or isostearic acid, to form an ammonium salt and the product is isolated by distilling off the solvent at atmospheric or reduced pressure. Depending upon the molecular weight and ethylene oxide content of the copolymer, it may be a viscous oil or a wax.

It is also possible to isolate un-neutralized copolymer and then proceed with neutralization (as described above) or quaternization of the amino groups. Quaternization reaction of the amines typically involves common alkylating agents, such as alkyl halides or sulfates, and the resulting quaternium salts may offer improved deposition properties or static electicity control as compared to the starting amines or their salts.

An alternative way to produce quaternized structures is to react the epoxy end-blocked polysiloxanes and epoxy end-blocked polyalkyleneoxides with secondary amines selected, for example, from diethylamine, dipropylamine, dibutylamine, diisobutylamine, dihexylamine, dicyclohexylamine, dibenzylamine, dipropanolamine, and the like in the presence of a stoichiometric amount of a Brönsted acid, such as hydrochloric acid, sulfuric acid or acetic acid. The reaction is carried out in a suitable solvent, such as an alcohol or a mixture of alcohol and water at reflux.

C. Copolymer Uses

The copolymers of the present invention are primarily intended as softeners for substrates, especially hair, fibers, and textiles. While these copolymers can be used neat, for ease of application, they are usually applied to the substrates dissolved, dispersed, or emulsified in a suitable liquid medium. Preferably, they are applied to the substrate from an aqueous solution, emulsion, or suspension. They may also be applied as a solution in a non-aqueous solvent, such as isopropanol, or in a liquid in which the copolymer is miscible. More preferably, the copolymer is applied to the substrate as an aqueous dispersion.

Aqueous emulsions of the copolymers can be prepared by combining the copolymer with one or more emulsifiers, such as nonionic surfactants, and diluted with water to a desired concentration. Nonionic surfactants commonly employed in such emulsions can include, for example, TERGITOL surfactants, available from Union Carbide Chemicals and Plastics Co., Inc.

Stable aqueous dispersions of the copolymers can, for example, be prepared by directly blending or mixing a solution of the copolymer in a water miscible solvent, such as isopropanol, propylene glycol, dipropylene glycol, or dipropylene glycol methyl ether, with water to obtain the desired copolymer level.

Once prepared, the dispersions, emulsions, or solutions can be applied to a substrate by any conventional means, such as by spraying, dipping, kiss roll application, or other application method typically employed in fiber, hair, or textile treatment. The substrates that can be treated with the copolymers of the present invention are exemplified by natural fibers, such as hair, cotton, silk, flax, cellulose, paper (including tissue paper), and wool; synthetic fibers, such as polyester, polyamide, polyacrylonitrile, polyethylene, polypropylene, and polyurethane; and inorganic fibers, such as glass or carbon fibers. Fabric substrates that can be treated with the copolymers of the present invention are exemplified by fabrics produced from the above-mentioned fibrous materials or blends thereof.

In general, the dispersions, emulsions, or solutions are applied to hair, fiber, or textile substrates such that up to 5 percent, preferably 0.25 to 2.5 percent of the copolymer by weight of the dry substrate remains on the substrate. Optionally, other additives commonly used to treat hair or textile substrates can be employed along with the copolymers of the present invention, including but not limited to, additional surfactants, deposition polymers, quaternary conditioning agents, curing resins, preservatives, dyes, colorants, formularies, and the like.

Moreover, compositions comprising the copolymers of the present invention can be used in personal care formulations, including cleansers, body washes, soaps, lotions, creams, shaving cream, hair sprays, conditioners, shampoos, deodorants, moisturizers, sunblocks, and the like.

The copolymers of the present invention can be formulated into these and other products together with one or more anionic surfactants, one or more amphoteric surfactants, one or more nonionic surfactants, and/or one or more deposition polymers or thickeners.

Suitable anionic surfactants include sulfonated and sulfated alkyl, aralkyl, and alkaryl anionic compounds; alkyl succinates; alkyl sulfosuccinates; N-alkanoyl sarcosinates; and the like. Preferred are the sodium, magnesium, ammonium, and the mono-, di- and triethanolamine salts of alkaryl sulfonates. The alkyl groups preferably contain 8 to 22 carbon atoms. Sulfate ethers are contemplated, preferably containing 1 to 10 ethylene oxide and/or propylene oxide units. Preferred examples of anionic surfactants include sodium lauryl sulfate, sodium lauryl ether sulfate, ammonium lauryl sulfate, triethanolamine lauryl sulfate, sodium $C_{14-16}$ olefin sulfonates, ammonium pareth-25 sulfate, sodium myristyl ether sulfate, ammonium lauryl ether sulfate, disodium monooleamido-sulfosuccinate, ammonium lauryl sulfosuccinate, sodium dodecylbenzene sulfonate, triethanolamine dodecylbenzene sulfonate, sodium N-lauroyl sarcosinate, and the like.

Examples of amphoteric surfactants with which the copolymers of the present invention can be formulated include cocoamphocarboxyglycinate, cocoamphocarboxypropionate, cocobetaine, N-cocoamidopropyldimethylglycine, and N-lauryl-N'- carboxymethyl-N'-(2-hydroxyethyl)ethylenediamine, as well as the betaine and sultaine compounds disclosed in the CTFA Dictionary as useful in personal care products.

Examples of useful nonionic surfactants with which the copolymers of the present invention can be formulated include fatty acid mono- and dialkanolamides in which the fatty portion preferably contains from about 10 to about 21 carbon atoms, and amine oxides, such as N-alkyl amine oxides.

A typical shampoo formulation comprises from about 3 to about 30 weight percent of an anionic and/or amphoteric surfactant component, from about 0.1 to about 10 weight percent of a nonionic surfactant component, together with from about 0.1 to about 20 weight percent of one or more copolymers of the present invention, and water. The formulation also preferably comprises an effective amount, on the order of from about 0.1 to about 5 weight percent, of a thickener. Examples of suitable thickeners include, for example, sodium alginate, gum arabic, polyoxyethylene, guar gum, hydroxypropyl guar gum, cellulosics, such as methyl cellulose, methylhydroxypropyl cellulose, and hydroxypropylcellulose, starch derivatives, such as hydroxyethylamylose, locust bean gum, polysaccharides, and the like.

The advantages and the important features of the present invention will be more apparent from the following examples.

EXAMPLES

Example 1

Preparation of the Copolymers of the Invention

In a 1L 4-neck flask equipped with a mechanical stirrer, addition funnel, and reflux condenser, $\alpha,\omega$-hydrogensiloxane (charges provided in Table 1) of the general formula $HSi(CH_3)_2O\{Si(CH_3)_2O\}_p Si(CH_3)_2H$ was heated to 80° C. A slow addition of allyl glycidyl ether started at 80° C. after chloroplatinic acid (5 to 10 ppm as Pt) had been added to the flask. The temperature was maintained at 80 to 90° C. until no SiH could be detected. The excess allyl glycidyl ether was removed by vacuum stripping at 50 mm Hg and 120° C. The resulting epoxy end-blocked fluid was characterized by its epoxy equivalent weight.

Charges for the Preparation of the Epoxy End-blocked Polysiloxanes

| "p" | SiH Charge (g) | Allyl Glycidyl Ether Charge (g) | Designation of the Epoxy Fluid | Typical Epoxy Equivalent Weight (g) |
|---|---|---|---|---|
| 50 | 500 | 31.2 | E-I | 2127 |
| 100 | 500 | 15.9 | E-II | 3703 |

In a second step, the amine/amines of choice (detailed charges provided in Table 2), a sufficient amount of 2-propanol to make a 60 percent solution of the final copolymer, and 100 ppm of Vitamin E, were placed in a 1 L four-neck flask equipped with a stirrer, addition funnel, reflux condenser, and thermometer. The temperature of the reaction mixture was adjusted to 80° C. and $\alpha,\omega$-diepoxysiloxane and diepoxy- polyalkyleneoxide were added from the addition funnel, either at once or in two portions, allowing two hours between additions. After the reaction was complete (epoxy functionality was consumed), solvent was removed by distillation and the resulting fluid was used as is or after neutralization with acetic acid.

TABLE 2

Charges for the Preparation of the Copolymers

| | Copolymer I | Copolymer II | Copolymer III | Copolymer IV | Copolymer V |
|---|---|---|---|---|---|
| Epoxy-silicone | E-II | E-I | E-II | E-I | E-I |
| Charge of the Epoxy-silicone (g) | 701.6 | 400 | 140.2 | 159.6 | 160.0 |
| Epoxy-polyalkylene-oxide | DER 732 | DER 732 | DER 732 | DER 732 | DER 732 |
| Epoxy-polyalkylene-oxide charge (g) | 70.4 | 52.4 | 28.2 | 25.3 | 24.5 |
| Ethanolamine charge (g) | 13.1 | 11.2 | 4.4 | 4.8 | 5.4 |
| Diethanolamine charge (g) | 3.0 | 3.6 | — | — | — |
| Molar Excess of Amine | 10% | 22% | 10% | 5% | 18% |
| Appearance of the product | Milky | Hazy | Hazy | Clear | Clear |
| Viscosity (cps) | 12,600 | 12,800 | >50,000 | >50,000 | 26,700 |

Example 2

Testing Softening Properties of $(AB)_n A$ Copolymers

In this example, the test fabric and test procedures used were as follows:

Bleached Cotton Interlock Knit, Style 460 (Test Fabrics Inc., Middlesex N.J.)

Test Procedures

Conditioning Textiles for Testing, ASTM Method D-1776-79

Absorbency of Bleached Textiles, AATCC Method 79-1992

Softness evaluation was done by a hand panel and the tested fabrics were rated on a scale of from 1 to 10 (1 being the harshest).

Selected copolymers of the present invention (as dispersions in water) and MAGNASOFT SRS (control, commercial premium $(AB)_n$ polysiloxane aminopolyalkyleneoxide softener from OSi Specialties, Greenwich, Conn.) were applied to 100 percent cotton knit fabric from a pad bath. The softener concentration in the finishing composition was such that the effective add-on level on the fabric was 1 percent. Curing conditions were 171° C. for 1.5 minutes. Softening and absorbency data are summarized in Table 3.

TABLE 3

Softness Rating and Wettability

| Copolymer | Softness | Wetting Time (sec) |
|---|---|---|
| Magnasoft SRS | 5.75 | >90 |
| Copolymer I | 8.0 | 5.4 |
| Copolymer II | 7.75 | 2.6 |
| Copolymer III | 5.0 | 5.8 |
| Copolymer IV | 5.1 | 6.1 |

TABLE 3-continued

Softness Rating and Wettability

| Copolymer | Softness | Wetting Time (sec) |
|---|---|---|
| Copolymer V | 7.8 | 9.5 |
| Untreated Control | 1.25 | 0.2 |

Table 3 demonstrates that the non-$(AB)_n$ A copolymers of the present invention provide softening properties at least equivalent to, and wetting properties superior to, MAGNA-SOFT SRS silicone.

Example 3

Testing Hair Conditioning Properties

In a side-by-side comparison test, human hair was washed with a control shampoo and a conditioning shampoo containing either Silsoft A-843, an $(AB)_n$ type copolymer or the products of the present invention.

Hair Testing Procedure

Wet and dry combability are measured as the number of inches a comb travels when a 10-inch long hair tress, placed on a calibrated chart, is combed from top to bottom. Fly away is reported as the difference between the total width of the entire tress and the width of the hair bundle after the tress is combed quickly 10 times. Combability, appearance, and fly-away data are summarized in Table 4.

PREPARATION OF SHAMPOO

|  | Control (Wt %) | Conditioning (Wt %) |
|---|---|---|
| Ammonium Lauryl Sulfate, 28% | 35.0 | 35.0 |
| Lauramide DEA | 3.0 | 3.0 |
| PEG-120 Methyl Glucose Dioleate | 2.0 | 2.0 |
| "Glucamate" DOE-120[a] |  | 1.0 |
| Silicone Conditioning Ingredient |  |  |
| Citric Acid, anhydrous | 0.4 | 0.4 |
| Cocamidopropyl Betaine, 35% | 10.0 | 10.0 |
| Dimethicone Copolyol, SILWET ® surfactant L-7657[b] | 2.5 | 2.5 |
| Deionized Water | qs to 100 | qs to 100 |
| Preservative | qs | qs |

[a]Amerchol
[b]OSi Specialties, Inc.
The term "qs" means "quantity sufficient."

Procedure: Water was mixed with ammonium lauryl sulfate. The solution was heated to 45° C. and the remaining ingredients were added in the order listed, waiting for each ingredient to dissolve before adding the next. Preservative was added after cooling the formulation to room temperature.

TABLE 4

Properties of Hair

| TREAT-MENT | COMB-ABILITY WET (INCHES) | COMB-ABILITY DRY (INCHES) | FLY-AWAY (INCHES) | FEEL WET/DRY |
|---|---|---|---|---|
| Control Shampoo | 2.7 | 5.0 | 10.0 | Draggy/dry |
| Conditioning Shampoo with Copolymer I | 10 | 10 | 3.0 | Rich/Very silky soft |
| Conditioning Shampoo with Copolymer II | 10 | 10 | 2.5 | Rich/Very silky soft |
| Conditioning Shampoo with Copolymer III | 10 | 10 | 3.5 | Rich/Very silky soft |
| Conditioning Shampoo with Copolymer IV | 10 | 10 | 3.0 | Rich/Very silky soft |
| Conditioning Shampoo with Copolymer V | 10 | 10 | 3.0 | Rich/Very silky soft |
| Conditioning Shampoo with Silsoft A-843 | 6.5 | 9.5 | 3.5 | Dry/Silky soft |

Hair washed with the conditioning shampoo containing the conditioning ingredients of the present invention had improved wet and dry combability and the after feel as compared to Silsoft A-843 silicone copolymer.

In view of the many changes and modifications that can be made without departing from principles underlying the invention, reference should be made to the appended claims for an understanding of the scope of the protection to be afforded the invention.

What is claimed is:

1. A composition comprising non-hydrolyzable, block, non-$(AB)_n$ type copolymers comprising units of the formula $\{XR^2[(SiO(R^1)_2]_xSi(R^1)_2R^2X\}$, units of the formula $\{YO(C_aH_{2a}O)_bY\}$, and linking groups —$NR^3$—, wherein $R^1$ is alkyl, $R^2$ is a divalent organic moiety, X and Y are independently selected divalent organic groups formed by the ring opening of an epoxide, $R^3$ is selected from the group consisting of alkyl, aryl, aralkyl, oxygen-containing alkyl, oxygen-containing aryl, and oxygen-containing aralkyl, a=2 to 4, b=2 to 100, and x=1 to 500.

2. The composition of claim 1 wherein $R^1$ is an alkyl group having from one to four carbon atoms.

3. The composition of claim 1 wherein $R^2$ is a divalent hydrocarbon group comprising at least one carbon atom.

4. The composition of claim 3 wherein $R^2$ further comprises at least one hydroxy substituent thereon, at least one ether linkage, or a combination of at least one hydroxy substituent and at least one ether linkage.

5. The composition of claim 1 wherein the copolymers are end-capped with secondary amino groups —$NHR^3$ or tertiary amino groups —$NR^3R^4$, wherein $R^3$ and $R^4$ are independently selected from the group consisting of alkyl, aryl, aralkyl, oxygen-containing alkyl, oxygen-containing aryl, and oxygen-containing aralkyl.

6. The composition of claim 1 wherein X and Y and independently selected from the group consisting of —$CH_2CH(OH)(CH_2)_vCH(OH)CH_2$—, —$CH[CH_2OH](CH_2)_vCH[CH_2OH]$—, —$CH_2CH(OH)(CH_2)_vCH[CH_2OH]$—, —$(CH_2)_v$—$OCH_2CH(OH)CH_2$—, and —$(CH_2)_vOCH_2CH(CH_2[OH])$— wherein v=2 to 6.

7. The composition of claim 1 wherein the ring-opened epoxides are independently derived from members selected from the group consisting of:

ω(3,4-epoxycyclohexyl)alkylene, β-(3,4-epoxycyclohexyl)ethylene, β-(3,4-epoxycyclohexyl)-

β-methylethylene, and β-(3,4-epoxy-4-methylcyclohexyl)-β-methylethylene.

8. The composition of claim 1 wherein the polyoxyalkylene blocks represented by $(C_aH_{2a}O)$ are made up of ethylene oxide (a=2), propylene oxide (a=3), and butylene oxide (a=4) in a random or blocked fashion.

9. The composition of claim 1 wherein the amine groups are protonated or quaternized.

10. A method of making non-hydrolyzable, block, non-$(AB)_n$ type copolymers comprising units of the formula $\{XR^2[(SiO(R^1)_2]_cSi(R^1)_2R^2X\}$, units of the formula $\{YO(C_aH_{2a}O)_bY\}$, and linking groups —$NR^3$—, wherein $R^1$ is alkyl, $R^2$ is a divalent organic moiety, X and Y are independently selected divalent organic groups formed by the ring opening of an epoxide, $R^3$ is selected from the group consisting of alkyl, aryl, aralkyl, oxygen-containing alkyl, oxygen-containing aryl, and oxygen-containing aralkyl, a=2 to 4, b=2 to 100, and x=1 to 500, wherein the method comprises reacting (1) polysiloxanes of the formula $QR^2[(SiO(R^1)_2]_cSi(R^1)_2R^2Q$, and (2) polyalkyleneoxides of the formula $\{ZO(C_bH_{2b}O)_dZ\}$, wherein Q and Z are epoxide containing groups, with at least one primary amine or a combination of primary and secondary amines.

11. The method of claim 10 wherein $R^1$ is an alkyl group having from one to four carbon atoms.

12. The method of claim 10 wherein $R^2$ is a divalent hydrocarbon group comprising at least one carbon atom.

13. The method of claim 12 wherein $R^2$ further comprises at least one hydroxy substituent thereon, at least one ether linkage, or a combination of at least one hydroxy substituent and at least one ether linkage.

14. The method of claim 10 wherein the copolymers are end-capped with secondary amino groups —$NHR^3$ or tertiary amino groups —$NR^3R^4$, wherein $R^3$ and $R^4$ are independently selected from the group consisting of alkyl, aryl, aralkyl, oxygen-containing alkyl, oxygen-containing aryl, and oxygen-containing aralkyl.

15. The method of claim 10 wherein X and Y and independently selected from the group consisting of —$CH_2CH(OH)(CH_2)_vCH(OH)CH_2$—, —$CH[CH_2OH](CH_2)_vCH[CH_2OH]$—, —$CH_2CH(OH)(CH_2)_vCH[CH_2OH]$—, —$(CH_2)_v$—$OCH_2CH(OH)CH_2$—; and —$(CH2)_vOCH_2CH(CH_2[OH])$— wherein v=2 to 6.

16. The method of claim 10 wherein the ring-opened epoxides are independently derived from members selected from the group consisting of:

ω-(3,4-epoxycyclohexyl)alkylene, β-(3,4-epoxycyclohexyl)ethylene, β-(3,4-epoxycyclohexyl)-β-methylethylene, and β-(3,4-epoxy-4-methylcyclohexyl)-β-methylethylene.

17. The method of claim 10 wherein the the polyoxyalkylene blocks represented by $(C_aH_{2a}O)$ are made up of ethylene oxide (a=2), propylene oxide (a=3), and butylene oxide (a=4) in a random or blocked fashion.

18. The method of claim 10 wherein the amine groups are protonated or quaternized.

19. A method for softening a substrate comprising applying to said substrate a composition comprising non-hydrolyzable, block, non-$(AB)_n$ type copolymers comprising units of the formula $\{XR^2[(SiO(R^1)_2]_cSi(R^1)_2R^2X\}$, units of the formula $\{YO(C_aH_{2a}O)_bY\}$, and linking groups —$NR^3$—, wherein $R^1$ is alkyl, $R^2$ is a divalent organic moiety, X and Y are independently selected divalent organic groups formed by the ring opening of an epoxide, $R^3$ is selected from the group consisting of alkyl, aryl, aralkyl, oxygen-containing alkyl, oxygen-containing aryl, and oxygen-containing aralkyl, a=2 to 4, b=2 to 100, and x=1 to 500.

20. The method of claim 19 wherein $R^1$ is an alkyl group having from one to four carbon atoms.

21. The method of claim 19 wherein $R^2$ is a divalent hydrocarbon group comprising at least one carbon atom.

22. The method of claim 21 wherein $R^2$ further comprises at least one hydroxy substituent thereon, at least one ether linkage, or a combination of at least one hydroxy substituent and at least one ether linkage.

23. The method of claim 19 wherein the copolymers are end-capped with secondary amino groups —$NHR^3$ or tertiary amino groups —$NR^3R^4$, wherein $R^3$ and $R^4$ are independently selected from the group consisting of alkyl, aryl, aralkyl, oxygen-containing alkyl, oxygen-containing aryl, and oxygen-containing aralkyl.

24. The method of claim 19 wherein X and Y and independently selected from the group consisting of —$CH_2CH(OH)(CH_2)_vCH(OH)CH_2$—, —$CH[CH_2OH](CH_2)_vCH[CH_2OH]$—, —$CH_2CH(OH)(CH_2)_vCH[CH_2OH]$—, —$(CH_2)_v$—$OCH_2CH(OH)CH_2$—; and —$(CH2)_vOCH_2CH(CH_2[OH])$— wherein v=2 to 6.

25. The method of claim 19 wherein the ring-opened epoxides are independently derived from members selected from the group consisting of:

ω-(3,4-epoxycyclohexyl)alkylene, β-(3,4-epoxycyclohexyl)ethylene,

β-(3,4-epoxycyclohexyl)-β-methylethylene, and

β-(3,4-epoxy-4-methylcyclohexyl)-β-methylethylene.

26. The method of claim 19 wherein the the polyoxyalkylene blocks represented by $(C_aH_{2a}O)$ are made up of ethylene oxide (a=2), propylene oxide (a=3), and butylene oxide (a=4) in a random or blocked fashion.

27. The method of claim 19 wherein the amine groups are protonated or quaternized.

* * * * *